US005747998A

United States Patent [19]
Fowler et al.

[11] Patent Number: 5,747,998
[45] Date of Patent: May 5, 1998

[54] APPARATUS FOR DETECTING ANOMALIES IN PIPES

[75] Inventors: J. Thomas Fowler, Marblehead, Mass.; Steven S. Carroll, South Hampton, N.H.

[73] Assignee: Gas Research Institute, Chicago, Ill.

[*] Notice: The term of this patent shall not extend beyond the expiration date of Pat. No. 5,479,100.

[21] Appl. No.: 449,814

[22] Filed: May 24, 1995

Related U.S. Application Data

[62] Division of Ser. No. 241,031, May 10, 1994, Pat. No. 5,479,100.
[51] Int. Cl.⁶ .................. G01R 33/00; G01R 33/12; G01N 27/72; G01N 27/82
[52] U.S. Cl. .................. 324/263; 324/220
[58] Field of Search .................. 324/220, 263, 324/219, 221, 226, 238, 262

[56] References Cited

U.S. PATENT DOCUMENTS 3,209,243  9/1965  Walters et al. .................. 324/220
5,479,100  12/1995  Fowler et al. .................. 324/263

FOREIGN PATENT DOCUMENTS 2143331  2/1985  United Kingdom .................. 324/220

*Primary Examiner*—Walter E. Snow
*Attorney, Agent, or Firm*—Dick and Harris

[57] ABSTRACT

An apparatus and method for detecting anomalies in ferrous pipe structures is presented. An electrical current is passed through the ferrous pipe structure so as to create a magnetic field in the pipe. A sensor having one or more sensor shoe members is placed in the interior of a ferrous pipe structure to be inspected. Each sensor shoe member has one or more magnetometer elements for detecting the magnetic fields in the region of the ferrous pipe structure adjacent to which the sensor shoe member is placed.

6 Claims, 2 Drawing Sheets

APPARATUS FOR DETECTING ANOMALIES IN PIPES

This is a division of application Ser. No. 08/241,031, filed 10 May 94, now U.S. Pat. No. 5,479,100.

BACKGROUND OF THE INVENTION

1. Field of the Invention

The present invention relates to the field of apparatus and methods for detecting anomalies in ferrous pipe structures, such as natural gas or oil pipelines, through the use of magnetic sensors which are passed along the interior of the pipe structures.

2. The Prior Art

Piping systems, such as natural gas or oil piping systems, need to be inspected, after construction, and periodically after use has begun, for the purposes of detecting defects or points of failure or leakage, or in some cases, predicting such points of failure or leakage. Since such pipelines are typically buried or submerged, it has become necessary to develop a means for inspecting such pipe structures using preprogrammed robotic or remotely operated or teleoperated devices.

It is known, for example, that in ferrous pipe structures, such as are used for natural gas or petroleum, the pipe will have a residual or remnant magnetic field associated with it, which can be detected and measured by appropriate electromagnetic sensors placed next to or against the pipe structure. It is also known that by placing magnetic field sources next to such pipe structures, a portion of the magnetic flux from the sources can be forced to travel through the pipe structure. When sensors are activated to seek the imposed field(s;) passing through a pipe structure, if the particular local section of pipe is without welds, flaws or other anomalies, then the imposed fields will not be detected. If, however, the local section of pipe has welds, cracks, or other flaws or anomalies, then the imposed field will "leak" from the anomaly and be detected by the sensors, when the leakage field is compared to the profile of the residual or remnant field detected and measured for the same local portion of pipe.

Numerous examples of anomaly detection devices, using magnetic field generators and magnetic field sensor, exist in the prior art, including such devices as are disclosed in Beaver et al., U.S. Pat. No. 3,460,028; Barton, U.S. Pat. No. 3,593,122; Smith, U.S. Pat. No. 4,105,972; Birchak et al., U.S. Pat. No. 4,649,343; Ando et al., U.S. Pat. No. 4,742,298; and Cecco et al , U.S. Pat. No. 4,855,676.

The Beaver et al. '028 reference shows an anomaly detector having a single axially oriented magnetic field generating apparatus centrally arranged within the sensor rig. Annular brushes positioned fore and aft of a plurality of magnetic field sensor "sledges" on the sensor rig convey the magnetic field into and out of the pipe structure, such that the magnetic flux lines are parallel to the longitudinal axis of the pipe structure. The "sledges" are held in spring-biased relation against the interior surface of the pipe structure, as the sensor rig moves along the interior of the pipe structure.

The apparatus of the Barton '122 patent likewise employs fore and aft magnetic pole pieces to establish an axially extending magnetic flux path, with sensor "shoes" positioned axially between the pole pieces. An additional pole piece, positioned aft of the paired pole pieces, and having brush parts inclined relative to the interior surface of the pipe structure acts to strengthen the residual magnetic field in the pipe structure. The residual fields detected are compared to the readings taken when the pipe structure has the active magnetic field imposed upon it. The discrepancies in the two sets of readings indicates the presence of anomalies, which may be welds, or actual flaws in the pipe structure.

The Smith '972 patent shows a pipeline inspection vehicle having a plurality of sensor heads arranged in a circle about the vehicle, and held in place against the interior surface of the pipe structure by an annular, spring-biased structure. Each individual sensor head may have magnetic field generating apparatus therein, as well as magnetic field sensing apparatus.

The Birchak et al. '343 patent describes an inspection system for use in small bore tubes, in which a scanner body has two annular magnetic cores, arranged perpendicular to one another, inside a hollow core of the scanner body. An array of magnetic field sensors are arranged circumferentially around the scanner body. The field generated by the two magnetic cores, simultaneously, may be manipulated by phase shifting and amplitude variations, so as to shift the direction of the field, even to producing a helical magnetic flux, or to swing the flux through nearly 180° to expose an anomaly to magnetic flux directed normal to it.

The apparatus of the Ando et al. '298 patent employs an axially extending primary magnetic coil, and a plurality of circumferentially extending secondary coils positioned radially outwardly of the primary coil. The secondary coils do not impose a magnetic field, but rather sense the axial component of the magnetic flux generated by the primary coil, in the form of a voltage imposed on the secondary coil. The sensed component changes in the presence of a flaw positioned between the poles of the primary coil.

The Cecco et al. '676 reference shows an apparatus for inspection of a pipe, having a sensor member configured to produce both axially extending and radially extending magnetic fields, positioned along the length of the sensor member. The Cecco et al. reference describes that both fields are of such strength as to obtain very high levels of saturation in the pipe structure.

The present invention is particularly directed to inspection systems for ferrous pipe structures, which are particularly suited to small bore pipe structures, such as the piping systems for natural gas distribution, the pipes of which typically have a nominal four-inch interior diameter. Commonly, prior art defect detection systems, which have typically been configured for much larger diameter pipes, have relied upon detection techniques involving the complete saturation of the pipe structure by the generated magnetic fields. Such saturation involves substantial power consumption by electromagnets, or the use of large, typically heavy, permanent magnets.

To provide support, such as power cables and transformers or sufficiently powerful and durable portable power supplies for electromagnets, and/or conveyance mechanisms for the sensors for saturation-type detector devices, in the confined environment of a small-bore detector device, is a difficult task-. It is desirable, therefore, to provide a way of avoiding the logistical difficulties presented by saturation-type detector systems.

Particular problems are presented by anomalies which are closer to the outside surface of the pipe structure, such as cracks beginning from the outside, toward the interior of the pipe. As mentioned, due to space requirements, the power of the magnetic field generating means which can be carried on board the sensor is limited. Further, while the magnetometers which are carried on the sensor, are often carried in shoes which are held in a spring or mechanically biased manner against the inner surface of the pipe structure, there will still be an "air-gap" between the surface of the shoe and the pipe interior surface, across which the magnetic fields must jump to reach the pipe from the generators and return to the magnetometers. This gap, which may be only a few thousandths of an inch, is still enough to cause substantial attrition in the strength of the field being imposed upon the pipe, and subsequently being detected by the magnetometers.

An even more important potential problem is that the interior surfaces of gas pipes can be relatively irregular, with numerous bumps and ridges. This irregular surface forms part of the magnetic field circuit, causing variations in the emitted and sensed magnetic field. The irregularities thus become a source of error in the observed fluctuations of the magnetic field, as the sensor shoes pass over the interior surface of the pipe.

It is desirable, therefore, to provide a way of imposing a magnetic field into a pipe structure, without requiring large or complicated magnetic field generating devices to be carried by the sensor.

It is also desirable to provide a way of imposing a magnetic field into a pipe structure, which is suitable for use with sensors which are sized for small pipe diameter applications.

SUMMARY OF THE INVENTION

The invention is directed to an apparatus for detecting anomalies in a ferrous pipe structure, which comprises, in part, sensor means, for positioning within and movement along an interior of the ferrous pipe structure; means, operably associated with the sensor means, for imposing one or more magnetic fields into the ferrous pipe structure, the means for imposing one or more magnetic fields being operably disposed substantially externally to the pipe structure; means, operably associated with the sensor means, for detecting magnetic fields emanating from the ferrous pipe structure whether due to remnant induction in the ferrous pipe structure or to magnetic fields imposed by the means to impose magnetic fields; means for generating data signals corresponding to the magnetic fields detected by the means to detect magnetic fields; control means for receiving and processing the data signals generated by the sensor means, and for converting the data signals into information from which a user may determine the presence and characteristics of anomalies in the ferrous pipe structure; means for communicating the data signals generated by the sensor means to the control means; and means for propelling the sensor means along the interior of the ferrous pipe structure.

The means to impose magnetic fields comprises means for causing an electrical current to be passed through the ferrous pipe structure, so as to create a magnetic field in the pipe structure. In addition, the sensor means comprises a sensor support frame; at least one sensor shoe member, operably configured to be placed adjacent to an interior surface of the ferrous pipe structure; and means for operably positioning the at least one sensor shoe member adjacent to the interior surface of the ferrous pipe structure.

The means to detect magnetic fields in the ferrous pipe structure comprises at least one magnetometer operably disposed in the sensor shoe member, so as to detect magnetic fields emanating from the ferrous pipe structure.

The means for communicating the data signals generated by the sensor means to the control means comprises a hardwire connection from the sensor means to the control means. In an alternative embodiment of the invention, the means for communicating the data signals generated by the sensor means to the control means comprises telemetry means operably associated with the sensor means and the control means for transmitting the data signals from the sensor means to the control means without a hardwire connection therebetween. In a still further preferred embodiment of the invention, they comprise means for recording the data signals generated by the sensor means, for playback into the control means after retrieval of the sensor means from the interior of the ferrous pipe structure.

The invention also comprises a method for detecting anomalies in a ferrous pipe structure, of the kind employing an apparatus including a sensor to be positioned in and propelled along the interior of the ferrous pipe structure wherein the sensor includes at least one sensor shoe member, including the steps of a) placing the at least one sensor shoe member within the interior of the ferrous pipe structure at a desired location to be inspected; b) measuring any present remnant magnetic field within the ferrous pipe structure; c) imposing a first magnetic field, from an external source, onto the ferrous pipe structure and simultaneously measuring any magnetic field emanating from the ferrous pipe structure; d) imposing a second magnetic field of reversed polarity onto the ferrous pipe structure with the external source and simultaneously measuring any magnetic field emanating from the ferrous pipe structure; e) comparing the remnant magnetic field measured with the magnetic fields measured after imposition of the first, second, third and fourth magnetic fields to yield data representative of anomalies in the ferrous pipe structure at the desired location.

The steps of imposing a first magnetic field, from an external source, onto the ferrous pipe structure and simultaneously measuring any magnetic field emanating from the ferrous pipe structure; and imposing a second magnetic field of reversed polarity onto the ferrous pipe structure with the external source and simultaneously measuring any magnetic field emanating from the ferrous pipe structure, further comprise the steps of: a) providing a source of electrical current; b) connecting the source of electrical current to the pipe structure, at positions upstream and downstream from the desired location to be inspected; c) actuating the source of electrical current so as to cause electrical current to pass along the pipe structure through the desired location to be inspected; d) reversing the polarity of the source of electrical current, relative to the pipe structure and actuating the source of electrical current, so as to cause the current to flow in reverse direction through the pipe structure through the desired location to be inspected.

BEST MODE FOR CARRYING OUT THE INVENTION

Figure 1:
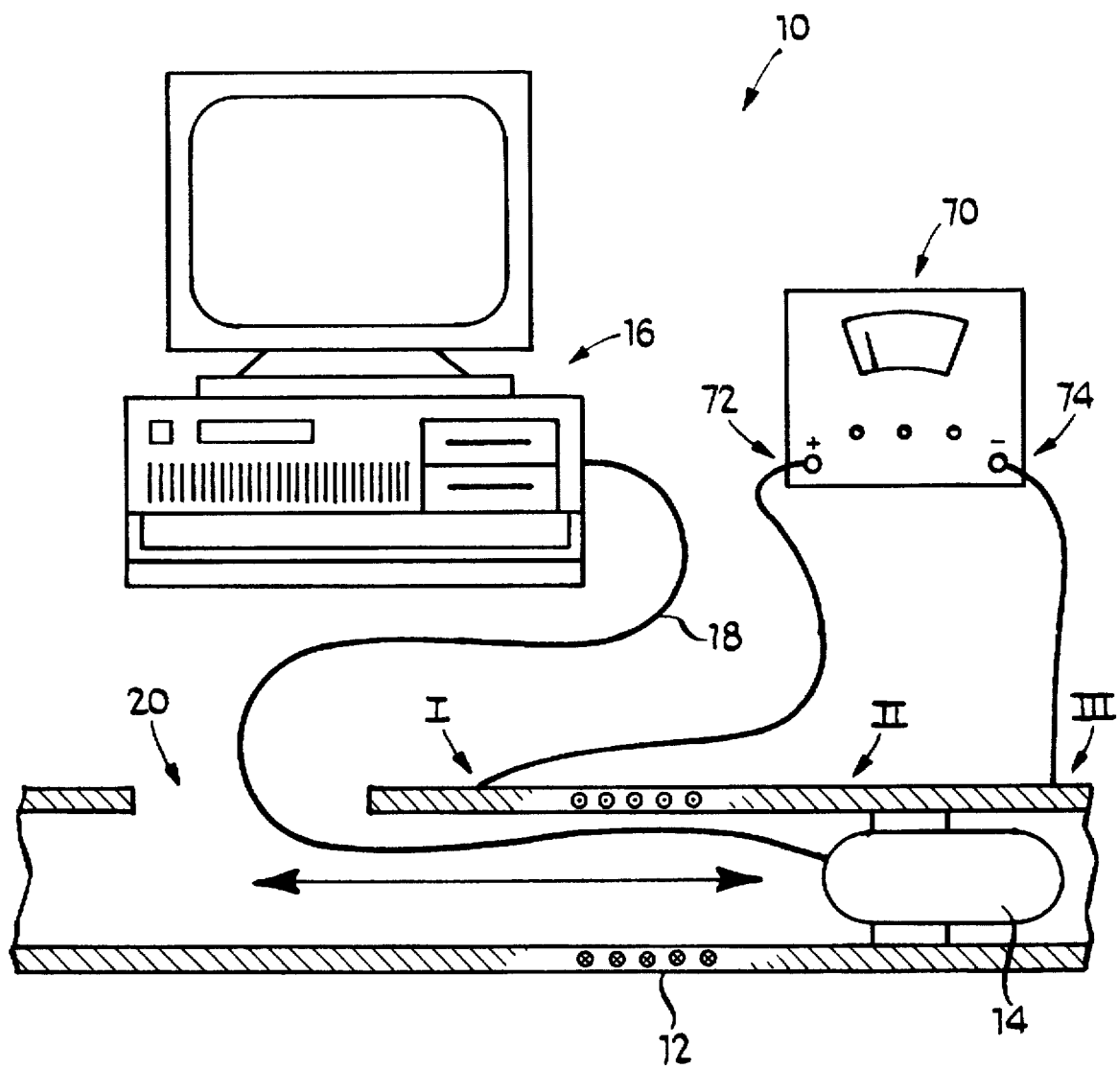
FIG. 1 is a schematic view of the apparatus for detecting anomalies in a pipe structure according to the present invention.

While the present invention is susceptible of embodiment in many different forms, there is shown in the drawings and will be described herein in detail, one specific embodiment, with the understanding that the present disclosure is to be considered as an exemplification of the principles of the invention, and is not intended to limit the invention to the embodiment illustrated.

FIG. 1 shows in schematic form, apparatus 10 for detecting anomalies in ferrous pipe structures, such as pipe structure 12. Apparatus 10 includes sensor 14, control computer 16, and a means for communication between sensor 14 and control computer 16. Although such communication means is shown in FIG. 1 as being represented by a hardwire connection 18, other types of communication, such as by telemetry, or by placement of a data storage device (not shown) in sensor 14, among others, for later playback of recorded data and downloading into control computer 16, are also contemplated.

In addition, sensor 14 must be provided with some form of propulsion back and forth along the interior of pipe structure 12. Sensor 14 may be moved by a push rod (not shown), examples of which are well known in the art, which may be externally controlled through breach 20 in pipe structure 12. Alternatively, sensor 14 may be attached to or constructed as part of a self-propelled robot crawler (not shown), examples of which are already known in the art.

Figure 2:
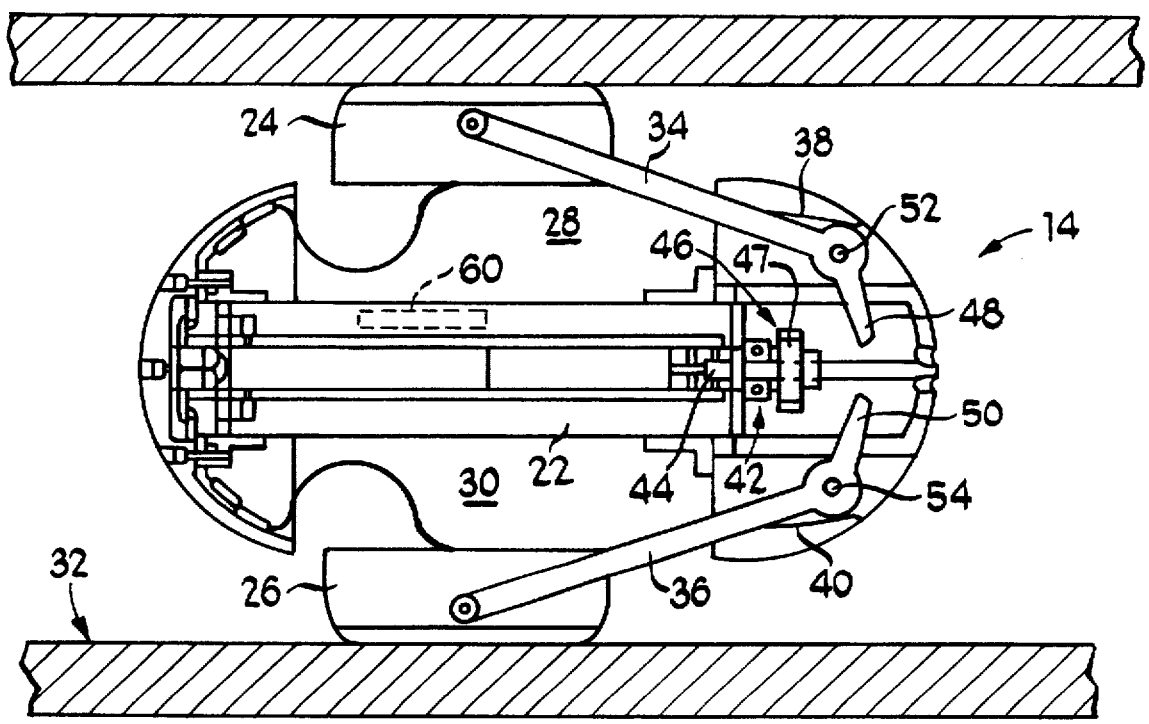
FIG. 2 is a side elevation, partially in section, of a sensor apparatus according to the present invention, shown with the sensor shoe members deployed against the inner surface of a pipe structure.

Sensor 14, shown in FIG. 2, includes sensor support frame 22 and sensor shoe members 24, 26. Sensor 14 may include a greater or lesser number of sensor shoe members, and preferably should have as many as possible arranged about the circumference of sensor 14, to provide as great a coverage of the surface of the pipe structure 12 as possible. Sensor shoe members 24, 26 are configured to be deployed from positions in pockets 28, 30, immediately adjacent to sensor support frame 22, to be held in a resiliently biased manner against the inner surface 32 of pipe structure 12.

Deployment and maintenance of sensor shoe members 24, 26 against inner surface 32 can be obtained by pivotably supporting sensor shoe members 24, 26 on arms 34, 36. Arms 34, 36 may be suitably biased, such as by springs 38, 40, so as to Lend to press sensor shoe members 24, 26 against inner surface 32. To retract arms 34, 36, a ballscrew mechanism 42, of any suitable known configuration, may be provided, such that upon actuation and rotation of the screw 44, for example by an electric motor, a ballnut 46 will be propelled axially in the direction of wings 48, 50 of arms 34, 36. Ballnut 46 will drive an actuator member 47 against wings 48, 50, causing arms 34, 36 to pivot about axes 52, 54, against the bias of springs 38, 40, thus withdrawing sensor shoe members 24, 26 back into pockets 28, 30. The deployment and retraction of sensor shoe members 24, 26 may also be used when sensor 14 must pass obstacles or restrictions in pipe structure 12.

Sensor support frame 22 of sensor 14 also provides space for the placement and protection of various electronic circuitry, as further discussed hereinafter.

Each sensor shoe member, such as sensor shoe member 24, is provided with a magnetometer apparatus, which may be a Hall Effect apparatus, a coil magnetometer, or, as in a preferred embodiment of the invention, a fluxgate magnetometer, which provides the advantages of smaller space requirements, smaller power requirements, and greater sensitivity. A multi-axis fluxgate magnetometer, such as a three-axis magnetometer, would be a preferred magnetic field sensor configuration, as it could be used to define the magnetic field as a resultant vector having components in each of three orthogonal coordinate axes.

In addition, each sensor shoe member may be provided with one or more magnetic field sources, such as permanent magnets, or electromagnets. Such a combination of elements will enable detection of a wide variety of anomalies in a pipe structure, particularly if the anomalies are on or near the inner surface of the pipe structure.

However, often the more significant, or more dangerous anomalies are cracks and hardspots which are in or near the outer surface of pipe structure. For example, if a crack has begun to propagate from the outer surface of the pipe structure, but has not breached the inner surface, the use of a combination of magnetic field sources and magnetometers, as previously described, may have some difficulty detecting the anomaly. There are several possible reasons for the difficulty.

Since there is no breach in the inner surface, the imposed magnetic field will only exit the pipe structure on the side of the breach, and the flux will then turn and enter the pipe structure. Therefore, the "leakage" field which the sensors could "see" would have to pass completely through the thickness of the pipe to be detected, and will present a rather weak signal. In addition, the use of sensor shoe members, even though pressed against the inner surface of the pipe structure, still does not provide a perfect mode of imposing the magnetic field, inasmuch as there is always a finite "air-gap" between the shoe member and the actual surface of the pipe.

The sensor shoes 24, in passing over the interior surface 32 of the pipe, pick up "noise" in the form of fluctuations in the imposed and magnetic fields due to the irregular, though not necessarily flawed, interior surface 32. This "noise" creates errors in the processing of the readings which should be avoided if possible. The "air-gap" also causes an attrition of the power of the imposed magnetic field. Although FIG. 2 is not intended to be to scale, it is accurate in that it reflects that while the sensor shoe members 24, 26 may appear, upon visual inspection to be in direct contact with the inner surface of pipe structure 12, there is in reality a space or "air-gap" of some few thousandths of an inch, which the magnetic fields being imposed and/or being sensed must cross, and that crossing takes power, which results in deterioration of the quality and detail of the readings obtained.

While it is not practical, in order to improve on the quality of detection of breaches and other anomalies which occur on the outer surface of the pipe structure, by using magnetometers on the outside of the pipe structure, a more powerful imposed magnetic field is desirable. To increase the power of the electromagnets would require larger and heavier cables and electromagnets, which would place an additional burden on the actual sensor transport system, particularly in a small diameter pipe inspection system. Likewise, the alternate use of larger, heavier permanent magnets is also not practical.

One way to impose a magnetic field in the pipe structure, of almost any desired flux strength, is to pass an electrical current through the pipe. Electrical current source 70, is shown in FIG. 1, schematically as an idealized source of current. The positive pole 72 is connected to pipe structure 12 at a position I, to one side of an inspection region II, and the negative pole 74 is connected to a position III, to the other side of inspection region II. Accordingly, the electrical "current" will flow in the direction of arrow C. In adherence to the "right-hand rule", a magnetic flux will be established which flows circumferentially in the pipe structure 12. As seen by the viewer in FIG. 1, the (x)'s indicate magnetic flux into the pipe, while the (·)'s indicate magnetic flux out of the pipe. The use of applied electrical current enables a very large magnetic flux to be created, which, in the case of "external" anomalies in the pipe structure, facilitates their detection from within the bore of the pipe.

A magnetometer (not shown), for example a three-axis fluxgate-type magnetometer, is part of a sensor package, which may be carried in each sensor shoe member 24, 26. Appropriate circuitry for driving the magnetometer, and for taking the analog signals generated by magnetometer, and converting them into digital data signals for processing by control computer 16, are located in sensor support frame 22.

As mentioned, the use of electrical current being supplied through the pipe directly may be used as an alternative to, or in addition to, magnetic fields imposed from within the pipe structure, for example from magnetic coils carried in the sensor shoe members. The internally carried magnetic field generation means may be in the form of a single coil, or a pair of coils arranged at right angles to one another. The magnetometer(s) may be positioned at the intersection of and between the poles of the magnetic coils.

The procedure for inspection of a particular local section of pipe structure is as follows. The sensor 14 is placed in the desired local section to be inspected. Sensor shoe members 24, 26 are in their deployed positions, against inner surface 32 of pipe structure 12. The magnetometer(s) measure(s) and map(s) the residual/remnant field in the local region of the pipe structure. If a multi-axis magnetometer is used, the measurements may be resolved into vectors having components in three orthogonal axes, for example, an X-axis, concentric with the longitudinal axis of the pipe structure, and Y- and Z-axes being normal both to the X-axis and each other.

The current source 70 is then actuated, in the configuration shown in FIG. 2, and a second set of readings are taken. If desired, the leads may be switched at source 70, and the source actuated again, so as to produce a current in a direction opposite to the configuration shown in FIG. 2, with a third set of readings being taken.

The current may be manipulated in other ways as well. Alternating or direct current may be used, which may produce distinct sorts of readings, for additional detail. In addition, the phase of alternating current may be varied, and direct current may be pulsed, to simulate alternating current. It is contemplated that currents of 10–20 amperes will be used. Although this procedure is expected to be used while the pipe is "live" with ongoing flow of gas or oil, the procedure is believed to be entirely safe, due to the absence of any combustion oxygen or any opportunities for an open spark.

The readings from the magnetometer, as previously mentioned, which typically are in the form of analog electrical signals, may be converted to digital data signals by an onboard analog-to-digital circuitry of known configuration, carried in central support portion 22 of sensor 14. This digital data may then be stored in an onboard recording device, such as digital memory, or may be immediately transmitted, via hardwire, or telemetry, if appropriate transmission circuitry is provided, (such as indicated generally in phantom at 60, in FIG. 2) to control computer 16. Once all the pertinent data for a particular inspection location have been recorded or transmitted, the sensor 14 may then be propelled to the next desired inspection location along pipe structure 12.

The data obtained by the inspection procedure may be processed through a comparison of the residual/remnant field readings at a particular inspection location, with the readings taken when the current(s) are flowing. Where defects or other anomalies occur, the superposition of the imposed fields upon the residual/remnant field can lead to known particular results which can suggest upon the type of anomaly which is found. For example, in general, anomalies such as welds or hard spots (which are more likely sites of possible future failure) may have different residual magnetism and a comparison of the residual and imposed fields is different than similar readings taken in the vicinity of, for example, cold worked regions, where the pipe may have been accidentally or intentionally bent, or dented, during installation.

The taking of measurements of residual and imposed fields, in particular, using the powerful imposed fields provided through running electrical current directly through the pipe being inspected, facilitates the detection of anomalies which are on the outer regions of the pipe structure, anomalies which are more difficult to detect with lower powered fields imposed from within the interior of the pipe by more conventional pipeline sensors.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An apparatus for detecting anomalies in a ferrous pipe structure, comprising:

sensor means for positioning within and movement along an interior of the ferrous pipe structure;

means operably associated with the sensor means for imposing one or more magnetic fields into the ferrous pipe structure, the means for imposing one or more magnetic fields being operably disposed substantially externally to the pipe structure, and including means for applying an electrical current directly to the pipe structure, so as to create a magnetic field in the ferrous pipe structure, said means for imposing one or more magnetic fields including means for imposing a first magnetic field, from an external source, onto the ferrous pipe structure and means for imposing a second magnetic field of reversed polarity relative to the first magnetic field, from an external source, onto the ferrous pipe structure;

means operably associated with the sensor means for detecting magnetic fields emanating from the ferrous pipe structure, whether due to remnant induction in the ferrous pipe structure or to magnetic fields imposed by the means to impose magnetic fields;

means for generating data signals corresponding to the magnetic fields detected by the means to detect magnetic fields;

control means for receiving and processing the data signals generated by the sensor means, and for converting the data signals into information from which a user may determine the presence and characteristics of anomalies in the ferrous pipe structure, including means for simultaneously measuring any magnetic fields emanating from the ferrous pipe structure as a result of an imposition of a magnetic field from the means for imposing a first magnetic field, from an external source, onto the ferrous pipe structure and means for simultaneously measuring any magnetic fields emanating from the ferrous pipe structure as a result of an imposition of a magnetic field from the means for imposing a second first magnetic field, from an external source, onto the ferrous pipe structure and means for comparing the remnant magnetic field measured with the magnetic fields measured after imposition of first and second magnetic fields to yield data representative of anomalies in the ferrous pipe structure at the desired location;

means for communicating the data signals generated by the sensor means to the control means; and means for propelling the sensor means along the interior of the ferrous pipe structure.

2. The apparatus for detecting anomalies in a ferrous pipe structure according to claim 1, wherein the sensor means comprises:

a sensor support frame;

at least one sensor shoe member, operably configured to be placed adjacent to an interior surface of the ferrous pipe structure; and means for operably positioning the at least one sensor shoe member adjacent to the interior surface of the ferrous pipe structure.

3. The apparatus for detecting anomalies in a ferrous pipe structure according to claim 2 wherein the means for detecting magnetic fields emanating from the ferrous pipe structure comprises:

a magnetometer operably disposed in the sensor shoe member, so as to detect magnetic fields emanating from the ferrous pipe structure.

4. The apparatus for detecting anomalies in a ferrous pipe structure according to claim 1, wherein the means for communicating the data signals generated by the sensor means to the control means comprises:

a hardwire connection from the sensor means to the control means.

5. The apparatus for detecting anomalies in a ferrous pipe structure according to claim 1, wherein the means for communicating the data signals generated by the sensor means to the control means comprises:

telemetry means operably associated with the sensor means and the control means for transmitting the data signals from the sensor means to the control means without a hardwire connection therebetween.

6. The apparatus for detecting anomalies in a ferrous pipe structure according to claim 1, wherein the means for communicating the data signals generated by the sensor means to the control means comprises:

means for recording the data signals generated by the sensor means, for playback into the control means after retrieval of the sensor means from the interior of the ferrous pipe structure.

* * * * *